(12) United States Patent
Kravtchenko et al.

(10) Patent No.: US 7,004,979 B2
(45) Date of Patent: Feb. 28, 2006

(54) DYEING COMPOSITION COMPRISING AT LEAST ONE DIAMINOPYRAZOLE OXIDATION BASE AND AT LEAST ONE PYRAZOLO-AZOLE COUPLING AGENT

(75) Inventors: Sylvain Kravtchenko, Asnières (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 77 days.

(21) Appl. No.: 10/490,868

(22) PCT Filed: Sep. 27, 2002

(86) PCT No.: PCT/FR02/03315

§ 371 (c)(1),
(2), (4) Date: Mar. 26, 2004

(87) PCT Pub. No.: WO03/028686

PCT Pub. Date: Apr. 10, 2003

(65) Prior Publication Data

US 2004/0237220 A1 Dec. 2, 2004

(30) Foreign Application Priority Data

Sep. 28, 2001 (FR) .................... 01 12530

(51) Int. Cl.
*A61K 7/13* (2006.01)
(52) U.S. Cl. .................. 8/405; 8/406; 8/407; 8/408; 8/410; 8/421; 8/423; 8/570; 8/573; 8/690; 8/692; 548/262.4; 548/372.5
(58) Field of Classification Search ............ 8/405, 8/406, 407, 408, 410, 421, 423, 570, 573, 8/690, 692; 548/262.4, 372.5
See application file for complete search history.

(56) References Cited

U.S. PATENT DOCUMENTS

| 5,534,267 | A | * | 7/1996 | Neunhoeffer et al. | ....... 424/701 |
| 5,663,366 | A | * | 9/1997 | Neunhoeffer et al. | .... 548/371.4 |
| 5,718,731 | A | * | 2/1998 | Loewe et al. | ................. 8/409 |
| 5,785,717 | A | | 7/1998 | Maubru et al. | ................ 8/409 |
| 6,197,071 | B1 | | 3/2001 | Diehl et al. | .................... 8/409 |
| 6,231,623 | B1 | | 5/2001 | Vidal et al. | .................... 8/409 |

FOREIGN PATENT DOCUMENTS

| DE | 23 59 399 | 6/1975 |
| DE | 38 43 892 | 6/1990 |
| DE | 41 33 957 | 4/1993 |
| DE | 42 34 885 | 4/1994 |
| DE | 195 43 988 | 5/1997 |
| DE | 196 43 059 | 4/1998 |
| DE | 196 46 609 | 5/1998 |
| DE | 199 26 377 | 12/2000 |
| EP | 0 692 245 | 1/1996 |
| EP | 0 770 375 | 5/1997 |
| EP | 0 923 929 | 6/1999 |
| FR | 2 586 913 | 3/1987 |
| FR | 2 733 749 | 11/1996 |
| FR | 2 750 048 | 12/1997 |
| FR | 2 801 308 | 5/2001 |
| GB | 1026978 | 4/1966 |
| GB | 1153196 | 5/1969 |
| JP | 63 169571 | 1/1987 |
| JP | 5 163124 | 6/1993 |
| WO | WO 94/08970 | 8/1990 |
| WO | WO 94/08969 | 4/1994 |
| WO | WO 96/15765 | 5/1996 |

OTHER PUBLICATIONS

J. H. P. Juffermanns et al.; "Selective Thermolysis Reactions of Bromo-1-nitro-1H-pyrazoles. Formation of 3-Nitro-1H- vs. 4-Nitro-1H-pyrazoles," The Journal of Organic Chemistry, 1986, 51, pp. 4656-4660.
K. J. Klebe et al.; "A Facile Synthesis of 3(5)-Aminopyrazoles," Synthesis, 1973, No. 5: May, pp. 294-295.
R. Huttel et al.; Chemische Berichte; 1955, Jan. 1988, pp. 1586-1590.
English language DERWENT abstract of FR 2801308.
English language DERWENT abstract of DE 2359399.
English language DERWENT abstract of JP 63 169571.
English language DERWENT abstract of JP 5 163124.
English language DERWENT abstract of EP 0 770 375.
English language DERWENT abstract of FR 2 750 048.
English language DERWENT abstract of DE 41 33 957.
English language DERWENT abstract off FR 2 733 749.
English language DERWENT abstract of DE 19543988.
English language DERWENT abstract of DE 42 34 885.
English language DERWENT abstract of FR 2 586 913.
English language DERWENT abstract of EP 0 692 245.
English language DERWENT abstract of DE 19643059.
English language DERWENT abstract of DE 3843892.
English language DERWENT abstract of EP 923 929.
English language DERWENT abstract of DE 19646609.
English language DERWENT abstract of DE 19926377.

* cited by examiner

Primary Examiner—Eisa Elhilo
(74) Attorney, Agent, or Firm—Finnegan, Henderson, Farabow, Garrett & Dunner LLP

(57) ABSTRACT

The invention relates to a dye composition comprising an oxidation base of the diaminopyrazole type and a pyrazolo-azole coupler.

The invention also relates to the use of this composition for dyeing keratin fibres and also to the dyeing process using this composition.

32 Claims, No Drawings

DYEING COMPOSITION COMPRISING AT LEAST ONE DIAMINOPYRAZOLE OXIDATION BASE AND AT LEAST ONE PYRAZOLO-AZOLE COUPLING AGENT

The invention relates to a dye composition comprising an oxidation base of the diaminopyrazole type and a pyrazolo-azole coupler.

The invention also relates to the use of this composition for dyeing keratin fibres and also to the dyeing process using this composition.

It is known practice to dye keratin fibres and in particular human hair with dye compositions containing oxidation dye precursors, generally known as oxidation bases, such as ortho- or para-phenylene-diamines, ortho- or para-aminophenols and heterocyclic compounds. These oxidation bases are colourless or weakly coloured compounds, which, when combined with oxidizing products, may give rise to coloured compounds by a process of oxidative condensation.

It is also known that the shades obtained with these oxidation bases may be varied by combining them with couplers or coloration modifiers, the latter being chosen especially from aromatic meta-diamines, meta-aminophenols, meta-diphenols and certain heterocyclic compounds such as indole compounds.

The variety of molecules used as oxidation bases and couplers allows a wide range of colours to be obtained.

The "permanent" coloration obtained by means of these oxidation dyes must moreover satisfy a certain number of requirements. Thus, it must have no toxicological drawbacks, it must allow shades to be obtained in the desired intensity, and it must show good resistance to external agents such as light, bad weather, washing, permanent waving, perspiration and rubbing.

The dyes must also make it possible to cover white hair and, finally, they must be as unselective as possible, i.e. they must produce the smallest possible colour differences along the same length of keratin fibre, which is generally differently sensitized (i.e. damaged) between its end and its root.

Dye compositions comprising diaminopyrazole derivatives as oxidation bases are already known. For example, patent application DE 3 843 892 describes dye compositions for dyeing keratin fibres, comprising 4,5-diaminopyrazole derivatives that may be substituted in position 2 with alkyl or hydroxyalkyl radicals. Patent application EP 692 245 describes dye compositions comprising 4,5-diaminopyrazole derivatives combined with particular meta-phenylenediamines. Patent application DE 196 43 059 describes dye compositions combining 4,5-diaminopyrazole derivatives with meta-aminophenol and meta-phenylenediamine couplers. Patent application DE 196 46 609 describes dye compositions combining 4,5-diaminopyrazole derivatives with benzoxazine couplers.

It is furthermore known to use pyrazolo-azole compounds such as couplers in the presence of an oxidation base for dyeing keratin fibres, however, the shades obtained are not sufficiently strong, chromatic and/or fast.

The aim of the present invention is to provide novel dye compositions for dyeing keratin fibres, containing diaminopyrazole derivatives, which do not have the drawbacks of those of the prior art. In particular, the aim of the present invention is to provide dye compositions containing diaminopyrazole derivatives that are relatively unselective and particularly fast, while at the same time being capable of generating intense colorations in varied shades which moreover change little according to different applications.

This aim is achieved with the present invention, one subject of which is a dye composition comprising, in a suitable dyeing medium:

at least one 4,5-diaminopyrazole oxidation base of formula (I) or the corresponding addition salts

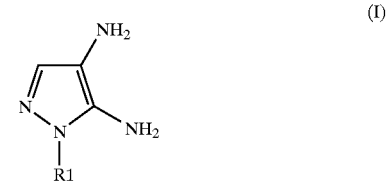

in which R1 is a $C_1-C_6$ alkyl radical substituted with one or more radicals OR, R being a $C_1-C_6$ alkyl radical;

at least one pyrazolo-azole coupler of formula (II), or the corresponding addition salts

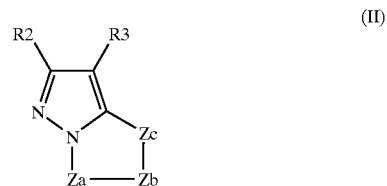

in which:

$R_2$ represents a hydrogen atom; a $C_1-C_{20}$ alkyl radical optionally substituted with one or two radicals R'; an aryl radical such as phenyl, benzyl or naphthyl, optionally substituted with one or two radicals R'; a 5- or 6-membered heterocyclic radical containing at least one nitrogen, oxygen or sulphur atom, such as pyridyl, quinolyl, pyrrolyl, morpholyl, furanyl, tetrahydrofuranyl, pyrazolyl, triazolyl, tetrazolyl, thiazolyl, oxazolyl, imidazolyl, thiophenyl, thienyl, furyl or thiadiazolyl, optionally substituted with one or two alkyl or R' radicals; a halogen atom, such as bromine, chlorine or fluorine; an acyl radical; a sulphonyl radical or an alkylsulphonyl radical; a sulphinyl radical; a phosphonyl radical; a carbamoyl radical; a sulphamoyl radical; a cyano radical; a siloxy radical; an amino radical; an acylamino radical; an acyloxy radical; a carbamoyloxy radical; a sulphonamido radical; an imido radical; a ureido radical; a sulphamoylamino radical; an alkoxycarbonylamino radical; an aryloxycarbonylamino radical; an alkoxycarbonyl radical; an aryloxycarbonyl radical; a carboxyl radical; a trifluoromethyl radical; when $R_2$ denotes an alkyl radical, an aryl radical or a 5- or 6-membered heterocycle, it may be linked to the carbon atom of the nucleus via an oxygen, nitrogen or sulphur atom (in this case, $R_2$ becomes $XR_2$ with X=O, NH or S);

R' is chosen from halogen, nitro, cyano, hydroxyl, alkoxy, aryloxy, amino, alkylamino, acylamino, carbamoyl, sulphonamido, sulphamoyl, imido, alkylthio, arylthio, aryl, alkoxycarbonyl or acyl radicals;

$R_3$ represents a hydrogen atom; a halogen atom such as bromine, chlorine or fluorine; an acetamido group; an alkylacetamido radical; an arylacetamido radical; an alkoxy radical such as methoxy, ethoxy, propyloxy, benzyloxy, methoxyethoxy, phenoxyethoxy, 2-cyanoethoxy, phenethyloxy, p-chlorobenzyloxy, methoxyethylcarbamoylmethoxy); an aryloxy radical optionally substituted with one or more radicals chosen from halogen, nitro, cyano, hydroxyl, alkoxy, amino, carbamoyl, imido, alkylthio, sulphonamido, alkylsulphonamido, sulphamoyl, alkoxy, carbonyl, carboxyl, alkylsulphonyl, methylenedioxy, acyl and alkyl radicals, for instance: phenyloxy, 4-methylphenoxy, 4-methoxyphenoxy, 4-nitrophenoxy, 4-cyanophenoxy, 4-methanesulphonamidophenoxy, 4-methanesulphonylphenoxy, 3-methylphenoxy, 1-naphthyloxy; an acyloxy radical optionally substituted with one or more radicals chosen from halogen, nitro, cyano, hydroxyl, alkoxy, amino, carbamoyl, imido, alkylthio, sulphonamido, sulphamoyl, alkoxy, carbonyl, carboxyl, alkylsulphonyl, methylenedioxy, aryl, alkyl, alkenyl and phenylalkenyl radicals, for instance acetoxy, propanoyloxy, benzoyloxy, 2,4-dichlorobenzoyloxy, ethoxyalkyloxy, pyruvyloyloxy, cinnamoyloxy or myristoyloxy; an arylthio radical optionally substituted with one or more radicals chosen from halogen, nitro, cyano, hydroxyl, alkoxy, amino, carbamoyl, imido, alkylthio, sulphonamido, sulphamoyl, alkoxy, carbonyl, carboxyl, alkylsulphonyl, methylenedioxy, acyl and alkyl radicals, for instance phenylthio, 4-methylphenylthio, 4-carboxyphenylthio, 2-ethoxy 5-tert-butylphenylthio, 2-tert-butylphenylthio 2-carboxyphenylthio and 4-methanesulphonylphenylthio; an alkylthio radical optionally substituted with one or more radicals chosen from halogen, nitro, cyano, hydroxyl, alkoxy, amino, alkyl or dialkylamino, carbamoyl, imido, alkylthio, sulphonamido, sulphamoyl, alkoxy, carbonyl, carboxyl, alkylsulphonyl, methylenedioxy, acyl, aryl and aralkyl radicals, for instance methylthio, ethylthio, propylthio, butylthio, 2-cyanoethylthio, benzylthio, phenethylthio, 2-(diethylamino) ethylthio, ethoxyethylthio or phenoxyethylthio; a heteroarylthio radical optionally substituted with one or more radicals chosen from halogen, nitro, cyano, hydroxyl, alkoxy, amino, carbamoyl, imido, alkylthio, sulphonamido, sulphamoyl, alkoxy, carbonyl, carboxyl, alkylsulphonyl, methylenedioxy, acyl and alkyl radicals, such as 5-phenyl-2,3,4,5-tetrazoylthio or 2-benzothiazolylthio; a heteroaryloxy radical optionally substituted with one or more radicals chosen from halogen, nitro, cyano, hydroxyl, alkoxy, amino, carbamoyl, imido, alkylthio, sulphonamido, sulphamoyl, alkoxy, carbonyl, carboxyl, alkylsulphonyl, methylenedioxy, acyl and alkyl radicals, such as 5-phenyl-2,3,4,5-tetrazolyloxy or 2-benzothiazolyloxy; a thiocyano radical; an N,N-diethylthiocarbonylthio radical; a dodecyloxythiocarbonylthio radical; a benzenesulphonamido radical; an N-ethyltoluenesulphonamido radical; a pentafluorobutanamido radical; a 2,3,4,5,6-pentafluorobenzamido radical; a p-cyanophenylureido radical; an N,N-diethylsulphamoylamino radical; a pyrazolyl radical; an imidazolyl radical; a triazolyl radical; a tetrazolyl radical; a benzimidazolyl radical; a 1-benzyl-5-ethoxy-3-hydantoinyl radical; a 1-benzyl-3-hydantoinyl radical; a 5,5-dimethyl-2,4-dioxo-3-oxazolidinyl radical; a 2-oxy-1,2-dihydro-1-pyridyl radical; an alkylamido radical; an arylamido radical; a radical $NR^{III}R^{IV}$, with $R^{III}$ and $R^{IV}$, which may be identical or different, representing a $C_1$–$C_4$ alkyl or a hydroxyalkyl radical; a carboxyl radical; an alkoxycarbonyl radical;

$Z_a$, $Z_b$ and $Z_C$ represent, independently of each other, a nitrogen atom or a carbon atom bearing a radical $R_4$ or $R_5$, which independently have the same meanings as those given for the radical $R_2$; $R_4$ and $R_5$ may also together form a substituted or unsubstituted aromatic ring, for instance phenyl or substituted phenyl, with the proviso that at least one of the radicals $Z_a$, $Z_b$ and $Z_c$ is other than a carbon atom.

Another subject of the invention is the use of the composition of the present invention for dyeing keratin fibres, in particular human keratin fibres such as the hair.

A subject of the invention is also a dyeing device and a dyeing process using the composition of the invention.

The composition of the present invention makes it possible in particular to obtain a chromatic, very strong, relatively unselective, and fast coloration of keratin fibres.

In the context of the present invention, the term "alkyl" means linear or branched radicals, for example methyl, ethyl, n-propyl, isopropyl, butyl, etc.

According to one particular embodiment, the 4,5-diaminopyrazole oxidation base of formula (I) is such that R1 represents a $C_1$–$C_4$ and preferably C2–C4 alkyl radical substituted with a radical OR, R being a $C_1$–$C_4$ and preferably C1–C2 alkyl radical.

Preferably, the oxidation base of formula (I) is 4,5-diamino-1-(2'-methoxyethyl)pyrazole.

According to one particular embodiment, the pyrazoloazole coupler of formula (II) of the present invention is such that R2 represents a hydrogen atom or a halogen atom; a $C_1$–$C_4$ alkyl; a phenyl radical optionally substituted with a C1–C4 alkyl, a halogen atom or a $C_1$–$C_4$ alkoxy radical; a benzyl radical; a $C_1$–$C_4$ hydroxyalkyl radical; an alkyl radical substituted with one or more halogen atoms; a $C_1$–$C_4$ aminoalkyl radical; a $C_1$–$C_4$ alkylamino radical; a $C_1$–$C_4$ dialkylamino radical; an alkoxy radical; an aryloxy radical; a carboxyl radical; a $C_1$–$C_4$ alkoxycarbonyl radical; a phenyloxy-carbonyl radical; an arylalkyl radical; an alkylthio radical; an arylthio radical; an alkylsulphonyl radical; a cyano radical; a heterocyclic radical.

By way of example, R2 represents a hydrogen, fluorine or chlorine atom; a methyl, ethyl, isopropyl, tert-butyl, phenyl, tolyl, 4-chlorophenyl, 4-methoxyphenyl, 3-methoxyphenyl, 2-methoxyphenyl, benzyl, trifluoromethyl, hydroxymethyl, aminomethyl, methoxy, ethoxy, phenoxy, methylamino, ethylamino, dimethylamino, carboxyl, methoxycarbonyl, ethoxycarbonyl, methylthio, ethylthio, phenylthio radical; a methanesulphonyl or cyano radical; a pyridyl, furyl or thienyl heterocycle. According to one particularly preferred embodiment, R2 represents a hydrogen or chlorine atom; a methyl, ethyl, phenyl, tolyl, 4-chlorophenyl, 4-methoxyphenyl, benzyl, trifluoromethyl, methoxy, ethoxy, carboxyl, methylamino, dimethylamino or cyano radical.

According to one embodiment, R3 represents a hydrogen atom; a $C_1$–$C_4$ alkoxy radical; a phenoxy radical; a phenoxy radical substituted with a halogen atom or a $C_1$–$C_4$ alkyl radical; a carboxyl radical; a trifluoromethyl radical; an acyloxy radical; a benzyloxy radical; a $C_1$–$C_4$ alkylthio radical; a phenylthio radical; a phenylthio radical substituted with a halogen atom, a $C_1$–$C_4$ alkyl, a carboxyl or a trifluoromethyl; a $C_1$–$C_4$ alkylamido radical; a phenylamido radical; a radical $NR^{III}R_{IV}$, a halogen atom.

By way of example, R3 represents a hydrogen, chlorine or bromine atom; a methoxy, ethoxy, phenyloxy, 4-methylphenyloxy, acyloxy, benzyloxy, methylthio, ethylthio, phenylthio, 4-methylphenylthio, 2-tert-butylphenylthio, acetamido, phenylacetamido, dimethylamino, diethylamino, ethylmethylamino or (β-hydroxyethyl)methylamino radical. Preferably, R3 represents a hydrogen or chlorine atom; an ethoxy, phenoxy, benzyloxy, acyloxy, acetamido or dimethylamino radical.

According to one embodiment, R4 and R5 each separately represents a hydrogen atom; a $C_1$–$C_4$ alkyl radical; a trifluoromethyl radical; a phenyl radical; a phenyl radical substituted with one or two radicals chosen from a halogen, a $C_1$–$C_4$ alkyl, $C_1$–$C_4$ alkoxy, hydroxyl, carboxyl, nitro, $C_1$–$C_4$ alkylthio, methylenedioxy, amino, trifluoromethyl or $C_1$–$C_4$ alkylamino radical; a benzyl radical; a benzyl radical substituted with a halogen atom or a methyl, isopropyl or methoxy radical; a $C_1$–$C_4$ hydroxyalkyl radical; a $C_1$–$C_4$ aminoalkyl radical; a $C_1$–$C_4$ alkylaminoalkyl radical; a C1–C4 alkoxy radical; a phenoxy radical; an alkylthio radical; a phenylthio radical; a methanesulphonyl radical; or R4 and R5 together form a phenyl radical, a phenyl radical substituted with a halogen, or a sulphonyl, $C_1$–$C_4$ alkoxy, $C_1$–$C_4$ alkyl, nitro, cyano, amino, alkylamino or trifluoromethyl radical.

By way of example, R4 and R5 each separately represent a hydrogen atom; a methyl, ethyl, isopropyl, n-propyl, tert-butyl, phenyl, tolyl, 2-, 3- or 4-chlorophenyl, 3- or 4-hydroxyphenyl, 3- or 4-aminophenyl, 3- or 4-methoxyphenyl, 4-trifluoromethylphenyl, benzyl, trifluoromethyl, hydroxymethyl, hydroxyethyl, hydroxyisopropyl, aminomethyl, aminoethyl, methoxy, ethoxy, methylthio or ethylthio radical; or R4 and R5 together form a phenyl, tolyl, sulphonylphenyl or chlorophenyl radical. Preferably, R4 and R5 each separately represent a hydrogen atom); a methyl, ethyl, isopropyl, phenyl, 4-chlorophenyl, 4-methoxyphenyl, 4-aminophenyl, methoxy, ethoxy, methylthio or ethylthio radical; or R4 and R5 together form a phenyl radical.

According to the present invention, the compounds of formula (II) are chosen from the following compounds:

(i) the pyrazolo[1,5-b]-1,2,4-triazoles of formula (IIa):

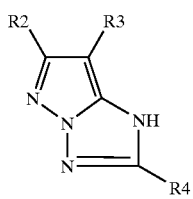

(ii) the pyrazolo[3,2-c]-1,2,4-triazoles of formula (IIb):

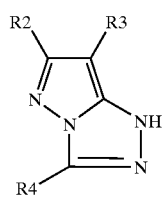

(iii) the pyrazolotetrazoles of formula (IIc):

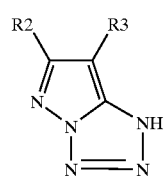

(iv) the pyrazolo[1,5-a]-imidazoles of formula (IId):

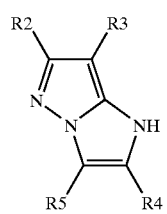

(v) the pyrazolo[5,1-e]-pyrazoles of formula (IIe):

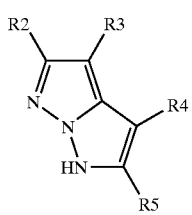

(vi) the pyrazolo[5,1-e]-1,2,3-triazoles of formula (IIf):

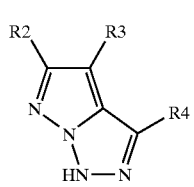

in which R2, R3, R4 and R5 are as defined above.

The compounds of formula (IIa) or (IIb) are chosen from those for which:

R2 denotes a hydrogen atom or a methyl, ethylthio, amino, trifluoromethyl, carboxyl, phenyl, ethoxy or cyano radical;

R3 denotes a hydrogen or chlorine atom;

R4 denotes a hydrogen atom or a methyl, ethyl, isopropyl, β-aminoethyl, β-hydroxyethyl, phenyl, methylthio or ethoxy radical.

The compounds of formula (IIc) are chosen from those for which:

R2 denotes a hydrogen atom or a methyl, trifluoromethyl, carboxyl, phenyl, ethoxy or cyano radical;

R3 denotes a hydrogen or chlorine atom.

The compounds of formula (IId) are chosen from those for which:
R2 denotes a hydrogen atom or a methyl, trifluoromethyl, amino, carboxyl, phenyl, ethoxy or cyano radical;
R3 denotes a hydrogen or chlorine atom;
R4 and R5 denote, respectively, hydrogen and hydrogen, hydrogen and methyl, methyl and hydrogen, hydrogen and amino, hydrogen and phenyl; or together form a phenyl.

The compounds of formula (IIe) are chosen from those for which:
R2 denotes a hydrogen atom or a methyl, trifluoromethyl, carboxyl, phenyl, ethoxy or cyano radical;
R3 denotes a hydrogen or chlorine atom;
R4 and R5 denote, respectively, hydrogen and methyl, methyl and hydrogen, methyl and methyl, or hydrogen and phenyl.

The compounds of formula (IIf) are chosen from those for which:
R2 denotes a hydrogen atom or a methyl, trifluoromethyl, carboxyl, phenyl, ethoxy or cyano radical;
R3 denotes a hydrogen or chlorine atom;
R4 denotes a hydrogen atom or a methyl radical.

The compounds of formula (II) are preferably chosen from:
2-methylpyrazolo[1,5-b]-1,2,4-triazole,
2-ethylpyrazolo[1,5-b]-1,2,4-triazole,
2-isopropylpyrazolo[1,5-b]-1,2,4-triazole,
2-phenylpyrazolo[1,5-b]-1,2,4-triazole,
2,6-dimethylpyrazolo[1,5-b]-1,2,4-triazole,
6-methyl-2-ethylpyrazolo[1,5-b]-1,2,4-triazole,
6-methyl-2-isopropylpyrazolo[1,5-b]-1,2,4-triazole,
6-methyl-2-phenylpyrazolo[1,5-b]-1,2,4-triazole,
6-carboxy-2-methylpyrazolo[1,5-b]-1,2,4-triazole,
6-carboxy-2-ethylpyrazolo[1,5-b]-1,2,4-triazole,
6-carboxy-2-isopropylpyrazolo[1,5-b]-1,2,4-triazole,
6-carboxy-2-phenylpyrazolo[1,5-b]-1,2,4-triazole,
6-phenyl-2-methylpyrazolo[1,5-b]-1,2,4-triazole,
6-phenyl-2-ethylpyrazolo[1,5-b]-1,2,4-triazole,
6-phenyl-2-isopropylpyrazolo[1,5-b]-1,2,4-triazole,
6-phenyl-2-phenylpyrazolo[1,5-b]-1,2,4-triazole,
6-amino-2-methylpyrazolo[1,5-b]-1,2,4-triazole,
6-amino-2-ethylpyrazolo[1,5-b]-1,2,4-triazole,
6-amino-2-isopropylpyrazolo[1,5-b]-1,2,4-triazole,
6-amino-2-phenylpyrazolo[1,5-b]-1,2,4-triazole,
6-ethylthio-2-methylpyrazolo[1,5-b]-1,2,4-triazole,
6-ethylthio-2-ethylpyrazolo[1,5-b]-1,2,4-triazole,
6-ethylthio-2-isopropylpyrazolo[1,5-b]-1,2,4-triazole,
6-ethylthio-2-phenylpyrazolo[1,5-b]-1,2,4-triazole,
6-ethoxy-2-methylpyrazolo[1,5-b]-1,2,4-triazole,
6-ethoxy-2-ethylpyrazolo[1,5-b]-1,2,4-triazole,
6-ethoxy-2-isopropylpyrazolo[1,5-b]-1,2,4-triazole,
6-ethoxy-2-phenylpyrazolo[1,5-b]-1,2,4-triazole,
6-methyl-2-(2'-aminoethyl)pyrazolo[1,5-b]-1,2,4-triazole,
6-carboxy-2-(2'-aminoethyl)pyrazolo[1,5-b]-1,2,4-triazole,
6-phenyl-2-(2'-aminoethyl)pyrazolo[1,5-b]-1,2,4-triazole,
6-ethylthio-2-(2'-aminoethyl)pyrazolo[1,5-b]-1,2,4-triazole,
2-(2'-aminoethyl)pyrazolo[1,5-b]-1,2,4-triazole,
2-(2'-hydroxyethyl)pyrazolo[1,5-b]-1,2,4-triazole,
6-methyl-2-(2'-hydroxyethyl)pyrazolo[1,5-b]-1,2,4-triazole,
6-ethylthio-2-(2'-hydroxyethyl)pyrazolo[1,5-b]-1,2,4-triazole,
6-carboxy-2-(2'-hydroxyethyl)pyrazolo[1,5-b]-1,2,4-triazole,
6-phenyl-2-(2'-hydroxyethyl)pyrazolo[1,5-b]-1,2,4-triazole,
7-chloro-2,6-dimethylpyrazolo[1,5-b]-1,2,4-triazole,
7-bromo-2,6-dimethylpyrazolo[1,5-b]-1,2,4-triazole,
3-methylpyrazolo[3,2-c]-1,2,4-triazole,
3-methylsulphinyl-6-phenylpyrazolo[3,2-c]-1,2,4-triazole,
3-ethylpyrazolo[3,2-c]-1,2,4-triazole,
3-isopropylpyrazolo[3,2-c]-1,2,4-triazole,
3-phenylpyrazolo[3,2-c]-1,2,4-triazole,
3-(2'-aminoethyl)pyrazolo[3,2-c]-1,2,4-triazole,
3-(2'-hydroxyethyl)pyrazolo[3,2-c]-1,2,4-triazole,
6-methyl-3-ethylpyrazolo[3,2-c]-1,2,4-triazole,
3,6-dimethylpyrazolo[3,2-c]-1,2,4-triazole,
6-methyl-3-isopropylpyrazolo[3,2-c]-1,2,4-triazole,
6-methyl-3-phenylpyrazolo[3,2-c]-1,2,4-triazole,
6-methyl-3-(2'-aminoethyl)pyrazolo[3,2-c]-1,2,4-triazole,
6-methyl-3-(2'-hydroxyethyl)pyrazolo[3,2-c]-1,2,4-triazole,
6-methyl-3-methylthiopyrazolo[3,2-c]-1,2,4-triazole,
6-phenyl-3-methylpyrazolo[3,2-c]-1,2,4-triazole,
6-phenyl-3-ethylpyrazolo[3,2-c]-1,2,4-triazole,
6-phenyl-3-isopropylpyrazolo[3,2-c]-1,2,4-triazole,
6-phenyl-3-phenylpyrazolo[3,2-c]-1,2,4-triazole,
6-phenyl-3-(2'-aminoethyl)pyrazolo[3,2-c]-1,2,4-triazole,
6-phenyl-3-(2'-hydroxyethyl)pyrazolo[3,2-c]-1,2,4-triazole,
6-phenyl-3-methylthiopyrazolo[3,2-c]-1,2,4-triazole,
6-ethylthio-3-methylpyrazolo[3,2-c]-1,2,4-triazole,
6-ethylthio-3-ethylpyrazolo[3,2-c]-1,2,4-triazole,
6-ethylthio-3-isopropylpyrazolo[3,2-c]-1,2,4-triazole,
6-ethylthio-3-phenylpyrazolo[3,2-c]-1,2,4-triazole,
6-ethylthio-3-(2'-aminoethyl)pyrazolo[3,2-c]-1,2,4-triazole,
6-ethylthio-3-(2'-hydroxyethyl)pyrazolo[3,2-c]-1,2,4-triazole,
6-trifluoromethyl-3-methylthiopyrazolo[3,2-c]-1,2,4-triazole,
6-trifluoromethylpyrazolo[3,2-c]-1,2,4-triazole,
6-carboxy-3-methylpyrazolo[3,2-c]-1,2,4-triazole,
6-carboxy-3-ethylpyrazolo[3,2-c]-1,2,4-triazole,
6-carboxy-3-isopropylpyrazolo[3,2-c]-1,2,4-triazole,
6-carboxy-3-phenylpyrazolo[3,2-c]-1,2,4-triazole,
6-carboxy-3-(2'-aminoethyl)pyrazolo[3,2-c]-1,2,4-triazole,
6-carboxy-3-(2'-hydroxyethyl)pyrazolo[3,2-c]-1,2,4-triazole,
7-chloro-3,6-dimethylpyrazolo[3,2-c]-1,2,4-triazole,
7-methoxycarbonyl-3,6-dimethylpyrazolo[3,2-c]-1,2,4-triazole,
pyrazolo[5,1-e]tetrazole,
6-methylpyrazolo[5,1-e]tetrazole,
6-phenylpyrazolo[5,1-e]tetrazole,
6-carboxypyrazolo[5,1-e]tetrazole,
7-chloro-6-methylpyrazolo[5,1-e]tetrazole,
pyrazolo[1,5-a]imidazole,
2-methylpyrazolo[1,5-a]imidazole,
2-phenylpyrazolo[1,5-a]imidazole,
pyrazolo[1,5-a]benzimidazole,
6-methylpyrazolo[1,5-a]imidazole,
2,6-dimethylpyrazolo[1,5-a]imidazole,
6-methyl-2-phenylpyrazolo[1,5-a]imidazole,
6-methylpyrazolo[1,5-a]benzimidazole,
6-phenylpyrazolo[1,5-a]imidazole,
6-phenyl-2-methylpyrazolo[1,5-a]imidazole,
2,6-diphenylpyrazolo[1,5-a]imidazole,
6-phenylpyrazolo[1,5-a]benzimidazole,
6-carboxypyrazolo[1,5-a]imidazole,
6-carboxy-2-methylpyrazolo[1,5-a]imidazole,
6-carboxy-2-phenylpyrazolo[1,5-a]imidazole,
6-carboxypyrazolo[1,5-a]benzimidazole,
6-ethoxypyrazolo[1,5-a]imidazole,
6-ethoxy-2-methylpyrazolo[1,5-a]imidazole,
6-ethoxy-2-phenylpyrazolo[1,5-a]imidazole,
6-trifluoromethylpyrazolo[1,5-a]benzimidazole, 6-aminopyrazolo[1,5-a]imidazole,
6-amino-2-methylpyrazolo[1,5-a]imidazole,
6-amino-2-phenylpyrazolo[1,5-a]imidazole,
6-aminopyrazolo[1,5-a]benzimidazole,
6-ethylthiopyrazolo[1,5-a]imidazole,
6-ethylthio-2-methylpyrazolo[1,5-a]imidazole,
6-ethylthio-2-phenylpyrazolo[1,5-a]imidazole,
7-chloro-6-methylpyrazolo[1,5-a]imidazole,
7-chloro-6-methylpyrazolo[1,5-a]benzimidazole,
8-amino-4-methylpyrazolo[5,1-e]pyrazole,
8-amino-5-chloro-4-methylpyrazolo[5,1-e]pyrazole,
5-methylpyrazolo[5,1-e]-1,2,3-triazole,
5-methyl-6-chloropyrazolo[5,1-e]-1,2,3-triazole,
5-phenylpyrazolo[5,1-e]-1,2,3-triazole, and the addition salts thereof with an acid.

Among these couplers, particular mention may be made of meta-phenylenediamines, meta-aminophenols, meta-diphenols, naphthalenic couplers and heterocyclic couplers other than those mentioned above, and the addition salts thereof.

The composition of the present invention may also comprise one or more additional oxidation bases conventionally used in oxidation dyeing, other than those described above. By way of example, these additional oxidation bases are chosen from para-phenylenediamines, bis(phenyl)alkylenediamines, para-aminophenols, ortho-aminophenols and heterocyclic bases other than those described above, and the addition salts thereof.

Among the para-phenylenediamines which can be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylene-diamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above that are particularly preferred are para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-p-acetylaminoethyloxy-para-phenylenediamine, and the addition salts thereof with an acid are more particularly preferred.

Among the bis(phenyl)alkylenediamines which can be mentioned, for example, are N,N'-bis(β-hydroxyethyl)-N, N'-bis(4'-aminophenyl)-1,3-diaminopropanol, N,N'-bis(β-hydroxyethyl)-N,N'-bis(4'-aminophenyl)-ethylenediamine, N,N'-bis(4-aminophenyl)tetramethylenediamine, N,N'-bis (β-hydroxyethyl)-N,N'-bis(4-aminophenyl)tetramethylenediamine, N,N'-bis(4-methyl-aminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof with an acid.

Among the para-aminophenols which can be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol and 4-amino-2-fluorophenol, and the addition salts thereof with an acid.

Among the ortho-aminophenols which can be mentioned, for example, are 2-aminophenol, 2-amino-5-methylphenol, 2-amino-6-methylphenol and 5-acetamido-2-aminophenol, and the addition salts thereof with an acid.

Among the heterocyclic bases mention may be made, for example, of pyridine derivatives, pyrimidine derivatives and pyrazole derivatives.

Among the pyridine derivatives which may be mentioned are the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Other pyridine oxidation bases that are useful in the present invention are the 3-aminopyrazolo[1,5-a]pyridine oxidation bases or the addition salts thereof described, for example, in patent application FR 2 801 308. By way of example, mention may be made of pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid, 2-methoxypyrazolo[1,5-a]pyrid-3-ylamine; (3-aminopyrazolo[1,5-a]pyrid-7-yl)methanol; 2-(3-aminopyrazolo[ 1,5-a]pyrid-5-yl) ethanol; 2,3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)amino]-ethanol; 2-[(3-aminopyrazolo[1,5-a]pyrid-7-yl)(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol and also the addition salts thereof with an acid or with a base.

Among the pyrimidine derivatives which may be mentioned are the compounds described, for example, in German patent DE 2 359 399 or Japanese patents JP 88-169 571; JP 05 163 124; EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo-[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]-pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropyl-aminopyrazolo[1,5-a]pyrimidine, and the addition salts thereof with an acid and the tautomeric forms thereof, when a tautomeric equilibrium exists.

Among the pyrazole derivatives which may be mentioned are the compounds described in patents DE 3 843 892 and DE 4 133 957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

The oxidation base(s) present in the composition of the invention is (are) each generally present in an amount of between 0.001% and 10% by weight approximately relative to the total weight of the dye composition, and preferably between 0.005% and 6%.

The composition according to the invention may contain one or more couplers conventionally used for dyeing keratin fibres other than the pyrazolo-azole couplers described above.

Examples that may be mentioned include 2-methyl-5-aminophenol, 5-N-(β-hydroxyethyl)amino- 2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene and the addition salts thereof with an acid.

In the composition of the present invention, the coupler(s) is (are) generally present in an amount of between 0.001% and 10% by weight approximately relative to the total weight of the dye composition, and preferably between 0.005% and 6%.

In general, the addition salts of the oxidation bases and of the couplers that may be used in the context of the invention are chosen especially from the addition salts with an acid, such as the hydrochlorides, hydrobromides, sulphates, citrates, succinates, tartrates, lactates, tosylates, benzenesulphonates, phosphates and acetates, and the addition salts with a base, such as sodium hydroxide, potassium hydroxide, ammonia, amines or alkanolamines.

The dye composition in accordance with the invention may also contain one or more direct dyes that may be chosen especially from nitrobenzene dyes, azo direct dyes and methine direct dyes. The direct dyes may be of nonionic, anionic or cationic nature.

The medium that is suitable for dyeing, also known as the dye support, generally consists of water or a mixture of water and at least one organic solvent to dissolve the compounds which would not be sufficiently soluble in water. As organic solvent, mention may be made, for example, of $C_1$–$C_4$ lower alkanols, such as ethanol and isopropanol; polyols and polyol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, and mixtures thereof.

The solvents are present in proportions preferably of between 1% and 40% by weight approximately relative to the total weight of the dye composition, and even more preferably between 5% and 30% by weight approximately.

The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, and in particular anionic, cationic, nonionic or amphoteric associative polymeric thickeners, antioxidants, penetration agents, sequestering agents, fragrances, buffers, dispersing agents, packaging agents such as, for example, silicones, which may or may not be volatile or modified, film-forming agents, ceramides, preserving agents and opacifiers.

The above adjuvants are generally present in an amount for each of them of between 0.01% and 20% by weight relative to the weight of the composition.

Needless to say, a person skilled in the art will take care to select this or these optional additional compounds such that the advantageous properties intrinsically associated with the oxidation dye composition in accordance with the invention are not, or are not substantially, adversely affected by the addition(s) envisaged.

The pH of the dye composition in accordance with the invention is generally between about 3 and 12 and preferably between about 5 and 11. It may be adjusted to the desired value using acidifying or basifying agents usually used in the dyeing of keratin fibres, or alternatively using standard buffer systems.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which can be mentioned, for example, are aqueous ammonia, alkaline carbonates, alkanolamines such as mono-, di- and triethanolamine and derivatives thereof, sodium hydroxide, potassium hydroxide and the compounds of formula (III) below:

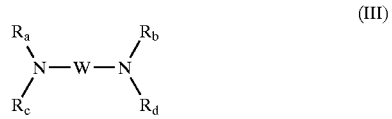

(III)

in which W is a propylene residue which is unsubstituted or substituted with a hydroxyl group or a $C_1$–$C_4$ alkyl radical; $R_a$, $R_b$, $R_c$ and $R_d$, which may be identical or different, represent a hydrogen atom, a $C_1$–$C_4$ alkyl radical or a $C_1$–$C_4$ hydroxyalkyl radical.

The dye composition according to the invention may be in various forms, such as in the form of liquids, creams or gels, or in any other form that is suitable for dyeing keratin fibres, and especially human hair.

According to the dyeing process of the present invention, the composition according to the present invention is applied to the fibres, and the colour is developed using an oxidizing agent. The colour may be developed at acidic, neutral or alkaline pH and the oxidizing agent may be mixed with the composition of the invention just at the time of use, or it may be used starting with an oxidizing composition containing it, which is applied simultaneously or sequentially to the composition of the invention.

According to one particular embodiment, the composition according to the present invention is mixed, preferably at the time of use, with a composition containing, in a medium that is suitable for dyeing, at least one oxidizing agent, this oxidizing agent being present in an amount that is sufficient to develop a coloration. The mixture obtained is then applied to the keratin fibres. After an action time of 3 to 50 minutes approximately, preferably 5 to 30 minutes approximately, the keratin fibres are rinsed, washed with shampoo, rinsed again and then dried.

The oxidizing agents conventionally used for the oxidation dyeing of keratin fibres are, for example, hydrogen peroxide, urea peroxide, alkali metal bromates, persalts such as perborates and persulphates, peracids and oxidase enzymes, among which mention may be made of peroxidases, 2-electron oxidoreductases such as uricases, and 4-electron oxygenases, for instance laccases. Hydrogen peroxide is particularly preferred.

The oxidizing composition may also contain various adjuvants conventionally used in compositions for dyeing the hair and as defined above for the composition of the invention.

The pH of the oxidizing composition containing the oxidizing agent is such that, after mixing with the dye composition, the pH of the resulting composition applied to the keratin fibres ranges between 3 and 12 approximately and preferably between 5 and 11. It may be adjusted to the desired value by means of acidifying or basifying agents usually used in the dyeing of keratin fibres and as defined above.

The ready-to-use composition that is finally applied to the keratin fibres may be in various forms, such as in the form of liquids, creams or gels or any other form that is suitable for dyeing keratin fibres, and especially human hair.

Another subject of the invention is a multi-compartment dyeing device or "kit", in which a first compartment contains the dye composition of the invention defined above and a second compartment contains an oxidizing composition. This device may be equipped with a means for applying the desired mixture to the hair, such as the devices described in patent FR-2 586 913 in the name of the Applicant.

The compounds that are useful in the composition of the present invention are known compounds that may be obtained using general preparation processes known to those skilled in the art. For example, the synthetic approach shown below is described in the literature up to the intermediate (2) (J. H. P. Juffermanns, C. L; Habraken; J. Org. Chem. 1986, 51, 4656; Klebe et al.; Synthesis, 1973, 294; R. Hüttel, F. Büchele; Chem. Ber.; 1955, 88, 1586). In the present case, the conversion of compound 3 into compound 2 is performed using an $NH_3$/EtOH mixture.

The alkylation and the amination to obtain the compounds of formula (1) according to the invention are mentioned in document DE 42 34 885.

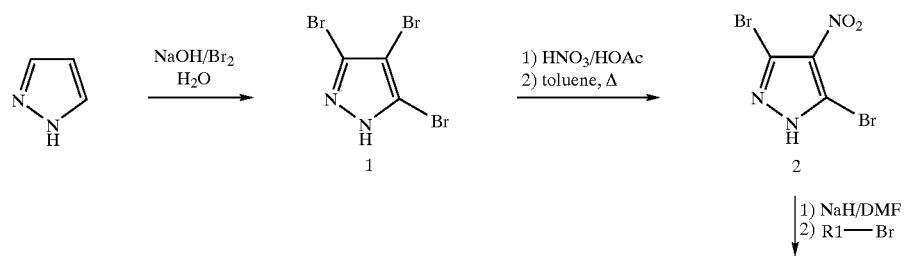

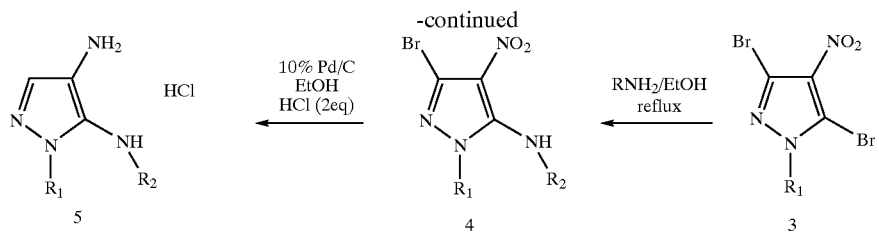

The examples that follow serve to illustrate the invention without, however, being limiting in nature.

EXAMPLES

Example 1

Synthesis of 4,5-diamino-1-(2'-methoxy-ethyl)pyrazole dihydrochloride

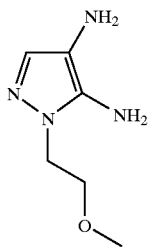

A mixture of 5-benzylamino-3-bromo-1-(2'-methoxyethyl)-4-nitropyrazole (4 g, 2.8 mmol) in ethanol (500 ml) containing a 10% Pd/C catalyst (Johnson-Mattey Type 487, dry weight 0.5 g) and 36% hydrochloric acid (0.57 g, 5.6 mmol) is hydrogenated in a Parr Autoclave (1 l) at 1 MPa for 1 hour. The catalyst is then removed by filtration and washed with ethanol, and the filtrate is evaporated under reduced pressure. A crude orange-coloured solid (2.8 g) is thus obtained, and is triturated in EtOAc (20 ml) for 1 hour. The solid is then filtered off and washed with cold EtOAc (20 ml) and then dried under vacuum to give the 4,5-diamino-1-(2'-methoxyethyl)pyrazole in the form of a beige-coloured solid (0.7 g, 27%).

HPLC (purity): 99.5% m.p.: 168.1–173.0° C.

$^1$H NMR: (400 MHz, d$^6$-DMSO): 7.34 (1H, s, NH$_{arom}$), 5.18 (1H, s$_{broad}$, NH), 4.09 (2H, t, J=5.5 Hz, CH$_2$N), 3.61 (2H, t, J=5.5 Hz, CH$_2$O), 3.23 (3H, s, OCH$_3$)

Example 2

Dye Composition Containing 4,5-diamino-1-(2'-methoxyethyl)pyrazole dihydrochloride The following dye composition was prepared:

| Example | 2 |
|---|---|
| 4,5-Diamino-1-(2'-methoxymethyl)-pyrazole 2HCl | 0.744 g |
| 3,6-dimethyl-2H-pyrazol[3,2-c]-1,2,4-triazole | 0.816 g |
| Dye support | (*) |
| Demineralized water q.s. | 100 g |

| Common dye support | |
|---|---|
| Benzyl alcohol | 2 g |
| Polyethylene glycol 8 EO | 3 g |
| Ethanol | 18 g |
| (C8–C10)alkyl polyglucoside as an aqueous solution containing 60% active material buffered with ammonium citrate, sold under the name Oramix CG110 by SEPPIC | 5 g in this case |
| Ammoniua at 20% NH$_3$ | 10 g |
| Sodium metabisulphite | 0.205 g |
| Sequestering agent | q.s. |

At the time of use, the composition is mixed with an equal weight of 20-volumes aqueous hydrogen peroxide solution (6% by weight).

The mixture obtained is applied to locks of natural and permanent-waved grey hair containing 90% white hairs, at a rate of 10 g per 1 g of hair. After an action time of 30 minutes, the locks are rinsed, washed with a standard shampoo, rinsed again and then dried.

The locks are assessed visually. An intense golden coloration is thus obtained.

What is claimed is:

1. A dye composition comprising, in a suitable dyeing medium:
    at least one oxidation base chosen from 4,5-diaminopyrazole oxidation bases of formula (I) and addition salts thereof

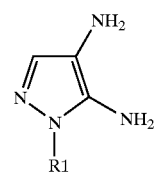

(I)

wherein R$_1$ is chosen from C$_1$–C$_6$ alkyl radicals substituted with at least one OR radical, wherein R is chosen from C$_1$–C$_6$ alkyl radicals; and at least one coupler chosen from pyrazolo-azole couplers of formula (II), and addition salts thereof

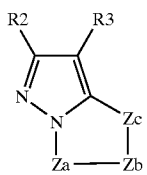

(II)

wherein:
- $R_2$ is chosen from hydrogen; $C_1$–$C_{20}$ alkyl radicals optionally substituted with one or two R' radicals; aryl radicals optionally substituted with one or two R' radicals; 5- and 6-membered heterocyclic radicals comprising at least one atom chosen from nitrogen, oxygen and sulphur atoms optionally substituted with one or two radicals chosen from alkyl and R' radicals; halogen atoms; acyl radicals; sulphonyl radicals; alkylsulphonyl radicals; sulphinyl radicals; phosphonyl radicals; carbamoyl radicals; sulphamoyl radicals; cyano radicals; siloxy radicals; amino radicals; acylamino radicals; acyloxy radicals; carbamoyloxy radicals; sulphonamido radicals; imido radicals; ureido radicals; sulphamoylamino radicals; alkoxycarbonylamino radicals; aryloxycarbonylamino radicals; alkoxycarbonyl radicals; aryloxycarbonyl radicals; carboxyl radicals; trifluoromethyl radicals;

wherein when $R_2$ is chosen from alkyl radicals, aryl radicals and 5- and 6-membered heterocycles, then $R_2$ may be linked to the carbon atom of the nucleus via an oxygen, nitrogen or sulphur atom;
- R' is a radical chosen from halogen, nitro, cyano, hydroxyl, alkoxy, aryloxy, amino, alkylamino, acylamino, carbamoyl, sulphonamido, sulphamoyl, imido, alkylthio, arylthio, aryl, alkoxycarbonyl and acyl radicals;
- $R_3$ is chosen from hydrogen; halogen atoms; acetamido groups; alkylacetamido radicals; arylacetamido radicals; alkoxy radicals; aryloxy radicals optionally substituted with at least one radical chosen from halogen, nitro, cyano, hydroxyl, alkoxy, amino, carbamoyl, imido, alkylthio, sulphonamido, alkylsulphonamido, sulphamoyl, alkoxy, carbonyl, carboxyl, alkylsulphonyl, methylenedioxy, acyl and alkyl radicals; acyloxy radicals optionally substituted with at least one radical chosen from halogen, nitro, cyano, hydroxyl, alkoxy, amino, carbamoyl, imido, alkylthio, sulphonamido, sulphamoyl, alkoxy, carbonyl, carboxyl, alkylsulphonyl, methylenedioxy, aryl, alkyl, alkenyl and phenylalkenyl radicals; arylthio radicals optionally substituted with at least one radical chosen from halogen, nitro, cyano, hydroxyl, alkoxy, amino, carbamoyl, imido, alkylthio, sulphonamido, sulphamoyl, alkoxy, carbonyl, carboxyl, alkylsulphonyl, methylenedioxy, acyl and alkyl radicals; alkylthio radicals optionally substituted with at least one radical chosen from halogen, nitro, cyano, hydroxyl, alkoxy, amino, alkyl and dialkylamino, carbamoyl, imido, alkylthio, sulphonamido, sulphamoyl, alkoxy, carbonyl, carboxyl, alkylsulphonyl, methylenedioxy, acyl, aryl and aralkyl radicals; heteroarylthio radicals optionally substituted with at least one radical chosen from halogen, nitro, cyano, hydroxyl, alkoxy, amino, carbamoyl, imido, alkylthio, sulphonamido, sulphamoyl, alkoxy, carbonyl, carboxyl, alkylsulphonyl, methylenedioxy, acyl and alkyl radicals; heteroaryloxy radicals optionally substituted with at least one radical chosen from halogen, nitro, cyano, hydroxyl, alkoxy, amino, carbamoyl, imido, alkylthio, sulphonamido, sulphamoyl, alkoxy, carbonyl, carboxyl, alkylsulphonyl, methylenedioxy, acyl and alkyl radicals; thiocyano radicals; N,N-diethylthiocarbonylthio radicals; dodecyloxythiocarbonylthio radicals; benzenesulphonamido radicals; N-ethyltoluenesulphonamido radicals; pentafluorobutanamido radicals; 2,3,4,5,6-pentafluorobenzamido radicals; p-cyanophenylureido radicals; N,N-diethylsulphamoylamino radicals; pyrazolyl radicals; imidazolyl radicals; triazolyl radicals; tetrazolyl radicals; benzimidazolyl radicals; 1-benzyl-5-ethoxy-3-hydantoinyl radicals; 1-benzyl-3-hydantoinyl radicals; 5,5-dimethyl-2,4-dioxo-3-oxazolidinyl radicals; 2-oxy-1,2-dihydro-1-pyridyl radicals; alkylamido radicals; arylamido radicals; $NR^{III}R^{IV}$ radicals, wherein $R^{III}$ and $R^{IV}$, which may be identical or different, are chosen from $C_1$–$C_4$ alkyls and hydroxyalkyl radicals; carboxyl radicals; alkoxycarbonyl radicals;
- $Z_a$, $Z_b$ and $Z_c$, which may be identical or different, are chosen from nitrogen atoms and carbon atoms bearing at least one radical chosen from $R_4$ and $R_5$,
- $R_4$ and $R_5$, which may be identical or different, are chosen from hydrogen; $C_1$–$C_{20}$ alkyl radicals optionally substituted with one or two R' radicals; aryl radicals optionally substituted with one or two R' radicals; 5- and 6-membered heterocyclic radicals comprising at least one atom chosen from nitrogen, oxygen and sulphur atoms optionally substituted with one or two radicals chosen from alkyl and R' radicals; halogen atoms; acyl radicals; sulphonyl radicals; alkylsulphonyl radicals; sulphinyl radicals; phosphonyl radicals; carbamoyl radicals; sulphamoyl radicals; cyano radicals; siloxy radicals; amino radicals; acylamino radicals; acyloxy radicals; carbamoyloxy radicals; sulphonamido radicals; imido radicals; ureido radicals; sulphamoylamino radicals; alkoxycarbonylamino radicals; aryloxycarbonylamino radicals; alkoxycarbonyl radicals; aryloxycarbonyl radicals; carboxyl radicals; and trifluoromethyl radicals;

wherein when either or both of $R_4$ or $R_5$ is chosen from alkyl radicals, aryl radicals and 5- and 6-membered heterocycles, then either or both of $R_4$ or $R_5$ may be linked to the carbon atom of the nucleus via an oxygen, nitrogen or sulphur atom;

$R_4$ and $R_5$ may also together form a substituted or unsubstituted aromatic ring, with the proviso that at least one of the radicals $Z_a$, $Z_b$ and $Z_c$ is other than a carbon atom.

2. The composition according to claim 1, wherein the substituted or unsubstituted aromatic ring formed by $R_4$ and $R_5$ is chosen from phenyl and substituted phenyl.

3. The composition according to claim 1, wherein in formula (I), $R_1$ is chosen from $C_1$–$C_4$ alkyl radicals substituted with at least one radical OR, wherein R is chosen from $C_1$–$C_4$ alkyl radicals.

4. The composition according to claim 1, wherein the at least one 4,5-diaminopyrazole oxidation base of formula (I) is 4,5-diamino-1-(2'-methoxyethyl)pyrazole.

5. The composition according to claim 1, wherein in formula (II), $R_2$ is chosen from hydrogen and halogen atoms; $C_1$–$C_4$ alkyls; phenyl radicals optionally substituted with at least one entity chosen from halogen atoms and $C_1$–$C_4$ alkyl and $C_1$–$C_4$ alkoxy radicals; benzyl radicals; $C_1$–$C_4$ hydroxyalkyl radicals; alkyl radicals substituted with at least one halogen atom; $C_1$–$C_4$ aminoalkyl radicals; $C_1$–$C_4$ alkylamino radicals; $C_1$–$C_4$ dialkylamino radicals; alkoxy radicals; aryloxy radicals; carboxyl radicals; $C_1$–$C_4$ alkoxycarbonyl radicals; phenyloxycarbonyl radicals; arylalkyl radicals; alkylthio radicals; arylthio radicals; alkylsulphonyl radicals; cyano radicals; and heterocyclic radicals.

6. The composition according to claim 5, wherein $R_2$ is chosen from hydrogen, fluorine and chlorine atoms; from methyl, ethyl, isopropyl, tert-butyl, phenyl, tolyl, 4-chlorophenyl, 4-methoxyphenyl, 3-methoxyphenyl, 2-methoxyphenyl, benzyl, trifluoromethyl, hydroxymethyl, aminomethyl, methoxy, ethoxy, phenoxy, methylamino, ethylamino, dimethylamino, carboxyl, methoxycarbonyl, ethoxycarbonyl, methylthio, ethylthio, phenylthio radicals; methanesulphonyl radicals; and cyano radicals; and from pyridyl, furyl and thienyl heterocycles.

7. The composition according to claim 6, wherein $R_2$ is chosen from hydrogen and chlorine atoms; methyl, ethyl, phenyl, tolyl, 4-chlorophenyl, 4-methoxyphenyl, benzyl, trifluoromethyl, methoxy, ethoxy, carboxyl, methylamino, dimethylamino and cyano radicals.

8. The composition according to claim 1, wherein in formula (II), $R_3$ is chosen from hydrogen; $C_1$–$C_4$ alkoxy radicals; phenoxy radicals; phenoxy radicals substituted with at least one entity chosen from halogen atoms and $C_1$–$C_4$ alkyl radicals; carboxyl radicals; trifluoromethyl radicals; acyloxy radicals; benzyloxy radicals; $C_1$–$C_4$ alkylthio radicals; phenylthio radicals; phenylthio radicals substituted with at least one entity chosen from halogen atoms, $C_1$–$C_4$ alkyl, carboxyl and trifluoromethyl radicals; $C_1$–$C_4$ alkylamido radicals; phenylamido radicals; radicals $NR'''R^{IV}$; and halogen atoms.

9. The composition according to claim 8, wherein $R_3$ is chosen from hydrogen, chlorine and bromine atoms; methoxy, ethoxy, phenyloxy, 4-methylphenyloxy, acyloxy, benzyloxy, methylthio, ethylthio, phenylthio, 4-methylphenylthio, 2-tert-butylphenylthio, acetamido, phenylacetamido, dimethylamino, diethylamino, ethylmethylamino and (β-hydroxyethyl)methylamino radicals.

10. The composition according to claim 9, wherein $R_3$ is chosen from hydrogen and chlorine atoms; ethoxy, phenoxy, benzyloxy, acyloxy, acetamido and dimethylamino radicals.

11. The composition according to claim 1, wherein in formula (II), $R_4$ and $R_5$, which may be identical or different, are chosen from hydrogen; $C_1$–$C_4$ alkyl radicals; trifluoromethyl radicals; phenyl radicals; phenyl radicals substituted with one or two radical chosen from halogen, $C_1$–$C_4$ alkyl, $C_1$–$C_4$ alkoxy, hydroxyl, carboxyl, nitro, $C_1$–$C_4$ alkylthio, methylenedioxy, amino, trifluoromethyl and $C_1$–$C_4$ alkylamino radicals; benzyl radicals; benzyl radicals substituted with at least one entity chosen from halogen atoms and methyl, isopropyl and methoxy radicals; $C_1$–$C_4$ hydroxyalkyl radicals; $C_1$–$C_4$ aminoalkyl radicals; $C_1$–$C_4$ alkylaminoalkyl radicals; $C_1$–$C_4$ alkoxy radicals; phenoxy radicals; aalkylthio radicals; phenylthio radicals; methanesulphonyl radicals; and $R_4$ and $R_5$ together can form at least one radical chosen from phenyl radicals, phenyl radicals substituted with at least one halogen, and sulphonyl, $C_1$–$C_4$ alkoxy, $C_1$–$C_4$ alkyl, nitro, cyano, amino, alkylamino and trifluoromethyl radicals.

12. The composition according to claim 11, wherein $R_4$ and $R_5$, which may be identical or different, are chosen from hydrogen; methyl, ethyl, isopropyl, n-propyl, tert-butyl, phenyl, tolyl, 2-, 3- and 4-chlorophenyl, 3- and 4-hydroxyphenyl, 3- and 4-aminophenyl, 3- and 4-methoxyphenyl, 4-trifluoromethylphenyl, benzyl, trifluoromethyl, hydroxymethyl, hydroxyethyl, hydroxyisopropyl, aminomethyl, aminoethyl, methoxy, ethoxy, methylthio and ethylthio radicals; and wherein $R_4$ and $R_5$ together can form at least one radical chosen from phenyl, tolyl, sulphonylphenyl and chlorophenyl radicals.

13. The composition according to claim 12, wherein $R_4$ and $R_5$, which may be identical or different, are chosen from hydrogen; methyl, ethyl, isopropyl, phenyl, 4-chlorophenyl, 4-methoxyphenyl, 4-aminophenyl, methoxy, ethoxy, methylthio and ethylthio radicals; and wherein $R_4$ and $R_5$ together can form a phenyl radical.

14. The composition according to claim 1, wherein the compounds of formula (II) are chosen from:

(i) pyrazolo[1,5-b]-1,2,4-triazoles of formula (IIa):

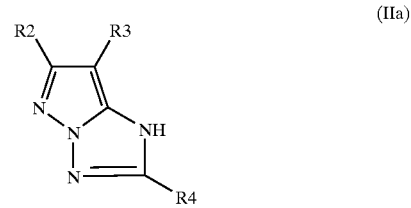

(ii) pyrazolo[3,2-c]-1,2,4-triazoles of formula (IIb):

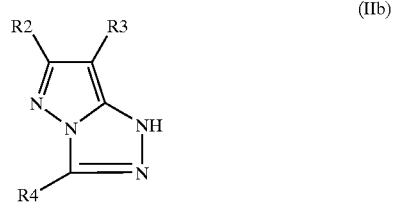

(iii) pyrazolotetrazoles of formula (IIc):

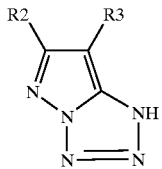

(iv) pyrazolo[1,5-a]imidazoles of formula (IId):

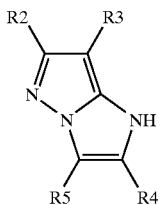

(v) pyrazolo[5,1-e]pyrazoles of formula (IIe):

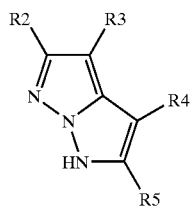

(vi) pyrazolo[5,1-e]-1,2,3-triazoles of formula (IIf):

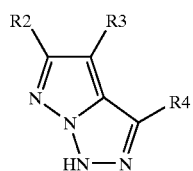

wherein $R_2$, $R_3$, $R_4$ and $R_5$, which may be identical or different, are defined as in claim 1; and addition salts thereof.

15. The composition according to claim 14, wherein the compounds of formula (IIa) or (IIb) are chosen from those wherein:
$R_2$ is chosen from hydrogen and methyl, ethylthio, amino, trifluoromethyl, carboxyl, phenyl, ethoxy and cyano radicals;
$R_3$ is chosen from hydrogen and chlorine atoms; and
$R_4$ is chosen from hydrogen and methyl, ethyl, isopropyl, β-aminoethyl, β-hydroxyethyl, phenyl, methylthio and ethoxy radicals.

16. The composition according to claim 14, wherein the compounds of formula (IIc) are chosen from those wherein:
$R_2$ is chosen from hydrogen and methyl, trifluoromethyl, carboxyl, phenyl, ethoxy and cyano radicals; and
$R_3$ is chosen from hydrogen and chlorine atoms.

17. The composition according to claim 14, wherein the compounds of formula (IId) are chosen from those wherein:
$R_2$ is chosen from hydrogen and methyl, trifluoromethyl, amino, carboxyl, phenyl, ethoxy and cyano radicals;
$R_3$ is chosen from hydrogen and chlorine atoms; and
$R_4$ and $R_5$, which may be identical or different, are chosen from, respectively, hydrogen and hydrogen, hydrogen and methyl, methyl and hydrogen, hydrogen and amino, or $R_4$ and $R_5$ together can form a phenyl radical.

18. The composition according to claim 14, wherein the compounds of formula (IIe) are chosen from those wherein:
$R_2$ is chosen from hydrogen and methyl, trifluoromethyl, carboxyl, phenyl, ethoxy and cyano radicals;
$R_3$ is chosen from hydrogen and chlorine atoms; and
$R_4$ and $R_5$, which may be identical or different, are chosen from, respectively, hydrogen and methyl, methyl and hydrogen, methyl and methyl, and hydrogen and phenyl radicals.

19. The composition according to claim 14, wherein the compounds of formula (IIf) are chosen from those wherein:
$R_2$ is chosen from hydrogen and methyl, trifluoromethyl, carboxyl, phenyl, ethoxy and cyano radicals;
$R_3$ is chosen from hydrogen and chlorine atoms; and
$R_4$ is chosen from hydrogen and methyl radicals.

20. The composition according to claim 1, wherein the compounds of formula (II) are chosen from:
2-methylpyrazolo[1,5-b]-1,2,4-triazole,
2-ethylpyrazolo[1,5-b]-1,2,4-triazole,
2-isopropylpyrazolo[1,5-b]-1,2,4-triazole,
2-phenylpyrazolo[1,5-b]-1,2,4-triazole,
2,6-dimethylpyrazolo[1,5-b]-1,2,4-triazole,
6-methyl-2-ethylpyrazolo[1,5-b]-1,2,4-triazole,
6-methyl-2-isopropylpyrazolo[1,5-b]-1,2,4-triazole,
6-methyl-2-phenylpyrazolo[1,5-b]-1,2,4-triazole,
6-carboxy-2-methylpyrazolo[1,5-b]-1,2,4-triazole,
6-carboxy-2-ethylpyrazolo[1,5-b]-1,2,4-triazole,
6-carboxy-2-isopropylpyrazolo[1,5-b]-1,2,4-triazole,
6-carboxy-2-phenylpyrazolo[1,5-b]-1,2,4-triazole,
6-phenyl-2-methylpyrazolo[1,5-b]-1,2,4-triazole,
6-phenyl-2-ethylpyrazolo[1,5-b]-1,2,4-triazole,
6-phenyl-2-isopropylpyrazolo[1,5-b]-1,2,4-triazole,
6-phenyl-2-phenylpyrazolo[1,5-b]-1,2,4-triazole,
6-amino-2-methylpyrazolo[1,5-b]-1,2,4-triazole,
6-amino-2-ethylpyrazolo[1,5-b]-1,2,4-triazole,
6-amino-2-isopropylpyrazolo[1,5-b]-1,2,4-triazole,
6-amino-2-phenylpyrazolo[1,5-b]-1,2,4-triazole,
6-ethylthio-2-methylpyrazolo[1,5-b]-1,2,4-triazole,
6-ethylthio-2-ethylpyrazolo[1,5-b]-1,2,4-triazole,
6-ethylthio-2-isopropylpyrazolo[1,5-b]-1,2,4-triazole,
6-ethylthio-2-phenylpyrazolo[1,5-b]-1,2,4-triazole,
6-ethoxy-2-methylpyrazolo[1,5-b]-1,2,4-triazole,
6-ethoxy-2-ethylpyrazolo[1,5-b]-1,2,4-triazole,
6-ethoxy-2-isopropylpyrazolo[1,5-b]-1,2,4-triazole,
6-ethoxy-2-phenylpyrazolo[1,5-b]-1,2,4-triazole,
6-methyl-2-(2'-aminoethyl)pyrazolo[1,5-b]-1,2,4-triazole,
6-carboxy-2-(2'-aminoethyl)pyrazolo[1,5-b]-1,2,4-triazole,
6-phenyl-2-(2'-aminoethyl)pyrazolo[1,5-b]-1,2,4-triazole,
6-ethylthio-2-(2'-aminoethyl)pyrazolo[1,5-b]-1,2,4-triazole,
2-(2'-aminoethyl)pyrazolo[1,5-b]-1,2,4-triazole,
2-(2'-hydroxyethyl)pyrazolo[1,5-b]-1,2,4-triazole,
6-methyl-2-(2'-hydroxyethyl)pyrazolo[1,5-b]-1,2,4-triazole, 6-ethylthio-2-(2'-hydroxyethyl)pyrazolo[1,5-b]-1,2,4-triazole,
6-carboxy-2-(2'-hydroxyethyl)pyrazolo[1,5-b]-1,2,4-triazole,
6-phenyl-2-(2'-hydroxyethyl)pyrazolo[1,5-b]-1,2,4-triazole,
7-chloro-2,6-dimethylpyrazolo[1,5-b]-1,2,4-triazole,
7-bromo-2,6-dimethylpyrazolo[1,5-b]-1,2,4-triazole,
3-methylpyrazolo[3,2-c]-1,2,4-triazole,
3-methylsulphinyl-6-phenylpyrazolo[3,2-c]-1,2,4-triazole,
3-ethylpyrazolo[3,2-c]-1,2,4-triazole,
3-isopropylpyrazolo[3,2-c]-1,2,4-triazole,
3-phenylpyrazolo[3,2-c]-1,2,4-triazole,
3-(2'-aminoethyl)pyrazolo[3,2-c]-1,2,4-triazole,
3-(2'-hydroxyethyl)pyrazolo[3,2-c]-1,2,4-triazole,
6-methyl-3-ethylpyrazolo[3,2-c]-1,2,4-triazole,
3,6-dimethylpyrazolo[3,2-c]-1,2,4-triazole,
6-methyl-3-isopropylpyrazolo[3,2-c]-1,2,4-triazole,
6-methyl-3-phenylpyrazolo[3,2-c]-1,2,4-triazole,
6-methyl-3-(2'-aminoethyl)pyrazolo[3,2-c]-1,2,4-triazole,
6-methyl-3-(2'-hydroxyethyl)pyrazolo[3,2-c]-1,2,4-triazole,
6-methyl-3-methylthiopyrazolo[3,2-c]-1,2,4-triazole
6-phenyl-3-methylpyrazolo[3,2-c]-1,2,4-triazole,
6-phenyl-3-ethylpyrazolo[3,2-c]-1,2,4-triazole,
6-phenyl-3-isopropylpyrazolo[3,2-c]-1,2,4-triazole,
6-phenyl-3-phenylpyrazolo[3,2-c]-1,2,4-triazole,
6-phenyl-3-(2'-aminoethyl)pyrazolo[3,2-c]-1,2,4-triazole,
6-phenyl-3-(2'-hydroxyethyl)pyrazolo[3,2-c]-1,2,4-triazole,
6-phenyl-3-methylthiopyrazolo[3,2-c]-1,2,4-triazole,
6-ethylthio-3-methylpyrazolo[3,2-c]-1,2,4-triazole,
6-ethylthio-3-ethylpyrazolo[3,2-c]-1,2,4-triazole,
6-ethylthio-3-isopropylpyrazolo[3,2-c]-1,2,4-triazole,
6-ethylthio-3-phenylpyrazolo[3,2-c]-1,2,4-triazole,
6-ethylthio-3-(2'-aminoethyl)pyrazolo[3,2-c]-1,2,4-triazole,
6-ethylthio-3-(2'-hydroxyethyl)pyrazolo[3,2-c]-1,2,4-triazole,
6-trifluoromethyl-3-methylthiopyrazolo[3,2-c]-1,2,4-triazole,
6-trifluoromethylpyrazolo[3,2-c]-1,2,4-triazole,
6-carboxy-3-methylpyrazolo[3,2-c]-1,2,4-triazole,
6-carboxy-3-ethylpyrazolo[3,2-c]-1,2,4-triazole,
6-carboxy-3-isopropylpyrazolo[3,2-c]-1,2,4-triazole,
6-carboxy-3-phenylpyrazolo[3,2-c]-1,2,4-triazole,
6-carboxy-3-(2'-aminoethyl)pyrazolo[3,2-c]-1,2,4-triazole,
6-carboxy-3-(2'-hydroxyethyl)pyrazolo[3,2-c]-1,2,4-triazole,
7-chloro-3,6-dimethylpyrazolo[3,2-c]-1,2,4-triazole,
7-methoxycarbonyl-3,6-dimethylpyrazolo[3 2-c]-1,2,4-triazole,
pyrazolo[5,1-e]tetrazole,
6-methylpyrazolo[5,1-e]tetrazole,
6-phenylpyrazolo[5,1-e]tetrazole,
6-carboxypyrazolo[5,1-e]tetrazole,
7-chloro-6-methylpyrazolo[5,1-e]tetrazole,
pyrazolo[1,5-a]imidazole,
2-methylpyrazolo[1,5-a]imidazole,
2-phenylpyrazolo[1,5-a]imidazole,
pyrazolo[1,5-a]benzimidazole,
6-methylpyrazolo[1,5-a]imidazole,
2,6-dimethylpyrazolo[1,5-a]imidazole,
6-methyl-2-phenylpyrazolo[1,5-a]imidazole,
6-methylpyrazolo[1,5-a]benzimidazole,
6-phenylpyrazolo[1,5-a]imidazole,
6-phenyl-2-methylpyrazolo[1,5-a]imidazole,
2,6-diphenylpyrazolo[1,5-a]imidazole,
6-phenylpyrazolo[1,5-a]benzimidazole,
6-carboxypyrazolo[1,5-a]imidazole,
6-carboxy-2-methylpyrazolo[1,5-a]imidazole,
6-carboxy-2-phenylpyrazolo[1,5-a]imidazole,
6-carboxypyrazolo[1,5-a]benzimidazole,
6-ethoxypyrazolo[1,5-a]imidazole,
6-ethoxy-2-methylpyrazolo[1,5-a]imidazole,
6-ethoxy-2-phenylpyrazolo[1,5-a]imidazole,
6-trifluoromethylpyrazolo[1,5-a]benzimidazole,
6-aminopyrazolo[1,5-a]imidazole,
6-amino-2-methylpyrazolo[1,5-a]imidazole,
6-amino-2-phenylpyrazolo[1,5-a]imidazole,
6-aminopyrazolo[1,5-a]benzimidazole,
6-ethylthiopyrazolo[1,5-a]imidazole,
6-ethylthio-2-methylpyrazolo[1,5-a]imidazole,
6-ethylthio-2-phenylpyrazolo[1,5-a]imidazole,
7-chloro-6-methylpyrazolo[1,5-a]imidazole,
7-chloro-6-methylpyrazolo[1,5-a]benzimidazole,
8-amino-4-methylpyrazolo[5,1-e]pyrazole,
8-amino-5-chloro-4-methylpyrazolo[5,1-e]pyrazole,
5-methylpyrazolo[5,1-e]-1,2,3-triazole,
5-methyl-6-chloropyrazolo[5,1-e]-1,2,3-triazole,
5-phenylpyrazolo[5,1-e]-1,2,3-triazole,
and addition salts thereof.

21. The composition according to claim 20, wherein the compounds of formula (II) are chosen from a compound having the following formula, and the addition salts thereof:

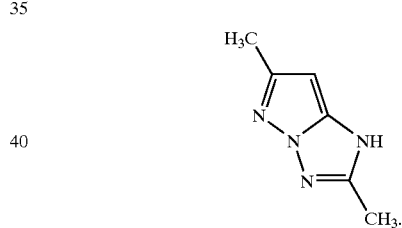

22. The composition according to claim 1, wherein the composition further comprises at least one additional oxidation base chosen from para-phenylenediamines, bis(phenyl)alkylenediamines, para-aminophenols, ortho-aminophenols and heterocyclic bases, other than the oxidation bases of formula (I), and addition salts thereof.

23. The composition according to claim 1, wherein the composition further comprises at least one additional coupler chosen from meta-phenylenediamines, meta-aminophenols, meta-diphenols, naphthalenic couplers and heterocyclic couplers other than the couplers of formula (II), and addition salts thereof.

24. The composition according to claim 1, wherein each of the oxidation bases is present in an amount ranging from 0.001% to 10% by weight, relative to the total weight of the dye composition.

25. The composition according to claim 1, wherein each of the couplers is present in an amount ranging from 0.001 to 10% by weight, relative to the total weight of the dye composition.

26. The composition according to claim 1, wherein the composition further comprises at least one oxidizing agent.

27. The composition according to claim 26, wherein the at least one oxidizing agent is chosen from hydrogen peroxide, urea peroxide, alkali metal bromates, persalts, peracids and oxidase enzymes.

28. A process for the oxidation dyeing of keratin fibers comprising
applying to the keratin fibers at least one dye composition, and developing color with at least one oxidizing agent,
wherein said at least one dye composition comprises, in a suitable dyeing medium:
at least one oxidation base chosen from 4,5-diaminopyrazole oxidation bases of formula (I) and addition salts thereof

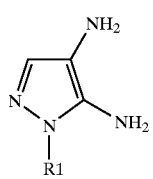
(I)

wherein $R_1$ is chosen from $C_1$–$C_6$ alkyl radicals substituted with at least one OR radical, wherein R is chosen from $C_1$–$C_6$ alkyl radicals; and
at least one coupler chosen from pyrazolo-azole couplers of formula (II), and addition salts thereof

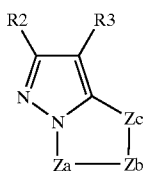
(II)

wherein:
$R_2$ is chosen from hydrogen; $C_1$–$C_{20}$ alkyl radicals optionally substituted with one or two R' radicals; aryl radicals optionally substituted with one or two R' radicals; 5- and 6-membered heterocyclic radicals comprising at least one atom chosen from nitrogen, oxygen and sulphur atoms optionally substituted with one or two radicals chosen from alkyl and R' radicals; halogen atoms; acyl radicals; sulphonyl radicals; alkylsulphonyl radicals; sulphinyl radicals; phosphonyl radicals; carbamoyl radicals; sulphamoyl radicals; cyano radicals; siloxy radicals; amino radicals; acylamino radicals; acyloxy radicals; carbamoyloxy radicals; sulphonamido radicals; imido radicals; ureido radicals; sulphamoylamino radicals; alkoxycarbonylamino radicals; aryloxycarbonylamino radicals; alkoxycarbonyl radicals; aryloxycarbonyl radicals; carboxyl radicals; and trifluoromethyl radicals;
wherein when $R_2$ is chosen from alkyl radicals, aryl radicals and 5- and 6-membered heterocycles, then $R_2$ may be linked to the carbon atom of the nucleus via an oxygen, nitrogen or sulphur atom;
R' is a radical chosen from halogen, nitro, cyano, hydroxyl, alkoxy, aryloxy, amino, alkylamino, acylamino, carbamoyl, sulphonamido, sulphamoyl, imido, alkylthio, arylthio, aryl, alkoxycarbonyl and acyl radicals;

$R_3$ is chosen from hydrogen; halogen atoms; acetamido groups; alkylacetamido radicals; arylacetamido radicals; alkoxy radicals; aryloxy radicals optionally substituted with at least one radical chosen from halogen, nitro, cyano, hydroxyl, alkoxy, amino, carbamoyl, imido, alkylthio, sulphonamido, alkylsulphonamido, sulphamoyl, alkoxy, carbonyl, carboxyl, alkylsulphonyl, methylenedioxy, acyl and alkyl radicals; acyloxy radicals optionally substituted with at least one radical chosen from halogen, nitro, cyano, hydroxyl, alkoxy, amino, carbamoyl, imido, alkylthio, sulphonamido, sulphamoyl, alkoxy, carbonyl, carboxyl, alkylsulphonyl, methylenedioxy, aryl, alkyl, alkenyl and phenylalkenyl radicals; arylthio radicals optionally substituted with at least one radical chosen from halogen, nitro, cyano, hydroxyl, alkoxy, amino, carbamoyl, imido, alkylthio, sulphonamido, sulphamoyl, alkoxy, carbonyl, carboxyl, alkylsulphonyl, methylenedioxy, acyl and alkyl radicals; alkylthio radicals optionally substituted with at least one radical chosen from halogen, nitro, cyano, hydroxyl, alkoxy, amino, alkyl and dialkylamino, carbamoyl, imido, alkylthio, sulphonamido, sulphamoyl, alkoxy, carbonyl, carboxyl, alkylsulphonyl, methylenedioxy, acyl, aryl and aralkyl radicals; heteroarylthio radicals optionally substituted with at least one radical chosen from halogen, nitro, cyano, hydroxyl, alkoxy, amino, carbamoyl, imido, alkylthio, sulphonamido, sulphamoyl, alkoxy, carbonyl, carboxyl, alkylsulphonyl, methylenedioxy, acyl and alkyl radicals; heteroaryloxy radicals optionally substituted with at least one radical chosen from halogen, nitro, cyano, hydroxyl, alkoxy, amino, carbamoyl, imido, alkylthio, sulphonamido, sulphamoyl, alkoxy, carbonyl, carboxyl, alkylsulphonyl, methylenedioxy, acyl and alkyl radicals; thiocyano radicals; N,N-diethylthiocarbonylthio radicals; dodecyloxythiocarbonylthio radicals; benzenesulphonamido radicals; N-ethyltoluenesulphonamido radicals; pentafluorobutanamido radicals; 2,3,4,5,6-pentafluorobenzamido radicals; p-cyanophenylureido radicals; N,N-diethylsulphamoylamino radicals; pyrazolyl radicals; imidazolyl radicals; triazolyl radicals; tetrazolyl radicals; benzimidazolyl radicals; 1-benzyl-5-ethoxy-3-hydantoinyl radicals; 1-benzyl-3-hydantoinyl radicals; 5,5-dimethyl-2,4-dioxo-3-oxazolidinyl radicals; 2-oxy-1,2-dihydro-1-pyridyl radicals; alkylamido radicals; arylamido radicals; $NR^{III}R^{IV}$ radicals, wherein $R^{III}$ and $R^{IV}$, which may be identical or different, are chosen from $C_1$–$C_4$ alkyls and hydroxyalkyl radicals; carboxyl radicals; alkoxycarbonyl radicals;

$Z_a$, $Z_b$ and $Z_c$, which may be identical or different, are chosen from nitrogen atoms and carbon atoms bearing at least one radical chosen from $R_4$ and $R_5$,
$R_4$ and $R_5$, which may be identical or different, are chosen from hydrogen; $C_1$–$C_{20}$ alkyl radicals optionally substituted with one or two R' radicals; aryl radicals optionally substituted with one or two R' radicals; 5- and 6-membered heterocyclic radicals comprising at least one atom chosen from nitrogen, oxygen and sulphur atoms optionally substituted with one or two radicals chosen from alkyl and R' radicals; halogen atoms; acyl radicals;

sulphonyl radicals; alkylsulphonyl radicals; sulphinyl radicals; phosphonyl radicals; carbamoyl radicals; sulphamoyl radicals; cyano radicals; siloxy radicals; amino radicals; acylamino radicals; acyloxy radicals; carbamoyloxy radicals; sulphonamido radicals; imido radicals; ureido radicals; sulphamoylamino radicals; alkoxycarbonylamino radicals; aryloxycarbonylamino radicals; alkoxycarbonyl radicals; aryloxycarbonyl radicals; carboxyl radicals; and trifluoromethyl radicals;

wherein when either or both of $R_4$ or $R_5$ is chosen from alkyl radicals, aryl radicals and 5- and 6-membered heterocycles, then either or both of $R_4$ or $R_5$ may be linked to the carbon atom of the nucleus via an oxygen, nitrogen or sulphur atom; $R_4$ and $R_5$ may also together form a substituted or unsubstituted aromatic ring, with the proviso that at least one of the radicals $Z_a$, $Z_b$ and $Z_c$ is other than a carbon atom.

29. The process according to claim 28, wherein the at least one oxidizing agent is chosen from hydrogen peroxide, urea peroxide, alkali metal bromates, persalts, peracids and oxidase enzymes.

30. The process according to claim 28, wherein, at the time of application, the at least one oxidizing agent is mixed with the at least one dye composition.

31. The process according to claim 28, wherein the at least one oxidizing agent is applied to the human keratin fibers in the form of an oxidizing composition, simultaneously or sequentially with the at least one dye composition.

32. A multi-compartment device, comprising at least one first compartment comprising at least one dye composition comprising, in a suitable dyeing medium:

at least one oxidation base chosen from 4,5-diaminopyrazole oxidation bases of formula (I) and addition salts thereof

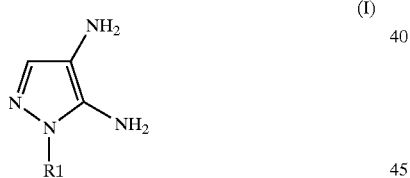

(I)

wherein $R_1$ is chosen from $C_1$–$C_6$ alkyl radicals substituted with at least one OR radical, wherein R is chosen from $C_1$–$C_6$ alkyl radicals; and at least one coupler chosen from pyrazolo-azole couplers of formula (II), and addition salts thereof

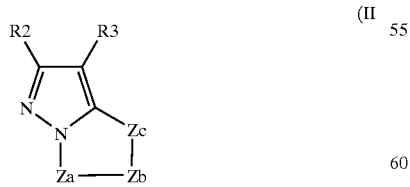

(II)

wherein:
$R_2$ is chosen from hydrogen; $C_1$–$C_{20}$ alkyl radicals optionally substituted with one or two R' radicals; aryl radicals optionally substituted with one or two R' radicals; 5- and 6-membered heterocyclic radicals comprising at least one atom chosen from nitrogen, oxygen and sulphur atoms optionally substituted with one or two radicals chosen from alkyl and R' radicals; halogen atoms; acyl radicals; sulphonyl radicals; alkylsulphonyl radicals; sulphinyl radicals; phosphonyl radicals; carbamoyl radicals; sulphamoyl radicals; cyano radicals; siloxy radicals; amino radicals; acylamino radicals; acyloxy radicals; carbamoyloxy radicals; sulphonamido radicals; imido radicals; ureido radicals; sulphamoylamino radicals; alkoxycarbonylamino radicals; aryloxycarbonylamino radicals; alkoxycarbonyl radicals; aryloxycarbonyl radicals; carboxyl radicals; and trifluoromethyl radicals;

wherein when $R_2$ is chosen from alkyl radicals, aryl radicals and 5- and 6-membered heterocycles, then $R_2$ may be linked to the carbon atom of the nucleus via an oxygen, nitrogen or sulphur atom;

R' is a radical chosen from halogen, nitro, cyano, hydroxyl, alkoxy, aryloxy, amino, alkylamino, acylamino, carbamoyl, sulphonamido, sulphamoyl, imido, alkylthio, arylthio, aryl, alkoxycarbonyl and acyl radicals;

$R_3$ is chosen from hydrogen; halogen atoms; acetamido groups; alkylacetamido radicals; arylacetamido radicals; alkoxy radicals; aryloxy radicals optionally substituted with at least one radical chosen from halogen, nitro, cyano, hydroxyl, alkoxy, amino, carbamoyl, imido, alkylthio, sulphonamido, alkylsulphonamido, sulphamoyl, alkoxy, carbonyl, carboxyl, alkylsulphonyl, methylenedioxy, acyl and alkyl radicals; acyloxy radicals optionally substituted with at least one radical chosen from halogen, nitro, cyano, hydroxyl, alkoxy, amino, carbamoyl, imido, alkylthio, sulphonamido, sulphamoyl, alkoxy, carbonyl, carboxyl, alkylsulphonyl, methylenedioxy, aryl, alkyl, alkenyl and phenylalkenyl radicals; arylthio radicals optionally substituted with at least one radical chosen from halogen, nitro, cyano, hydroxyl, alkoxy, amino, carbamoyl, imido, alkylthio, sulphonamido, sulphamoyl, alkoxy, carbonyl, carboxyl, alkylsulphonyl, methylenedioxy, acyl and alkyl radicals; alkylthio radicals optionally substituted with at least one radical chosen from halogen, nitro, cyano, hydroxyl, alkoxy, amino, alkyl and dialkylamino, carbamoyl, imido, alkylthio, sulphonamido, sulphamoyl, alkoxy, carbonyl, carboxyl, alkylsulphonyl, methylenedioxy, acyl, aryl and aralkyl radicals; heteroarylthio radicals optionally substituted with at least one radical chosen from halogen, nitro, cyano, hydroxyl, alkoxy, amino, carbamoyl, imido, alkylthio, sulphonamido, sulphamoyl, alkoxy, carbonyl, carboxyl, alkylsulphonyl, methylenedioxy, acyl and alkyl radicals; heteroaryloxy radicals optionally substituted with at least one radical chosen from halogen, nitro, cyano, hydroxyl, alkoxy, amino, carbamoyl, imido, alkylthio, sulphonamido, sulphamoyl, alkoxy, carbonyl, carboxyl, alkylsulphonyl, methylenedioxy, acyl and alkyl radicals; thiocyano radicals; N,N-diethylthiocarbonylthio radicals; dodecyloxythiocarbonylthio radicals; benzenesulphonamido radicals; N-ethyltoluenesulphonamido radicals; pentafluorobutanamido radicals; 2,3,4,5,6-pentafluorobenzamido radicals; p-cyanophenylureido radicals; N,N-diethylsulphamoylamino radicals; pyrazolyl radicals; imidazolyl radicals; triazolyl radicals; tetrazolyl radicals; benzimidazolyl radicals;

1-benzyl-5-ethoxy-3-hydantoinyl radicals; 1-benzyl-3-hydantoinyl radicals; 5,5-dimethyl-2,4-dioxo-3-oxazolidinyl radicals; 2-oxy-1,2-dihydro-1-pyridyl radicals; alkylamido radicals; arylamido radicals; $NR'''R^{IV}$ radicals, wherein $R^{III}$ and $R^{IV}$, which may be identical or different, are chosen from $C_1$–$C_4$ alkyls and hydroxyalkyl radicals; carboxyl radicals; alkoxycarbonyl radicals;

$Z_a$, $Z_b$ and $Z_c$, which may be identical or different, are chosen from nitrogen atoms and carbon atoms bearing at least one radical chosen from $R_4$ and $R_4$ and $R_5$, which may be identical or different, are chosen from hydrogen; $C_1$–$C_{20}$ alkyl radicals optionally substituted with one or two R' radicals; aryl radicals optionally substituted with one or two R' radicals; 5- and 6-membered heterocyclic radicals comprising at least one atom chosen from nitrogen, oxygen and sulphur atoms optionally substituted with one or two radicals chosen from alkyl and R' radicals; halogen atoms; acyl radicals; sulphonyl radicals; alkylsulphonyl radicals; sulphinyl radicals; phosphonyl radicals; carbamoyl radicals; sulphamoyl radicals; cyano radicals; siloxy radicals; amino radicals; acylamino radicals; acyloxy radicals; carbamoyloxy radicals; sulphonamido radicals; imido radicals; ureido radicals; sulphamoylamino radicals; alkoxycarbonylamino radicals; aryloxycarbonylamino radicals; alkoxycarbonyl radicals; aryloxycarbonyl radicals; carboxyl radicals; and trifluoromethyl radicals;

wherein when either or both of $R_4$ or $R_5$ is chosen from alkyl radicals, aryl radicals and 5- and 6-membered heterocycles, then either or both of $R_4$ or $R_5$ may be linked to the carbon atom of the nucleus via an oxygen, nitrogen or sulphur atom; $R_4$ and $R_5$ may also together form a substituted or unsubstituted aromatic ring, with the proviso that at least one of the radicals $Z_a$, $Z_b$ and $Z_c$ is other than a carbon atom and at least one second compartment comprising at least one oxidizing composition.

* * * * *

UNITED STATES PATENT AND TRADEMARK OFFICE
CERTIFICATE OF CORRECTION

PATENT NO. : 7,004,979 B2
DATED : February 28, 2006
INVENTOR(S) : Sylvain Kravtchenko and Alain Lagrange It is certified that error appears in the above-identified patent and that said Letters Patent is hereby corrected as shown below:

Column 20,
Line 1, "radical" should read -- radicals --.
Line 9, "aalkylthio" should read -- alkylthio --.

Column 22,
Line 49, "6-ethyithio-2-isopropylpyrazolo[1,5-b]-1,2,4-triazole," should read
-- 6-ethylthio-2-isopropylpyrazolo[1,5-b]-1,2,4-triazole, --.
Lines 62-63, "6-ethyithio-2-(2'-aminoethyl)pyrazolo[1,5-b]-1,2,4-triazole," should read
-- 6-ethylthio-2-(2'-aminoethyl)pyrazolo[1,5-b]-1,2,4-triazole, --.

Column 23,
Line 25, after "6-methyl-3-methylthiopyrazolo[3,2-c]-1,2,4-triazole" insert a comma.
Lines 54-55, "7-methoxycarbonyl-3,6-dimethylpyrazolo[3 2-c]-1,2,4-triazole," should
read -- 7-methoxycarbonyl-3,6-dimethylpyrazolo[3,2-c]-1,2,4-triazole, --.

Column 29,
Line 11, after "$R_4$ and" insert -- $R_5$, --.

Signed and Sealed this

Twenty-third Day of May, 2006

JON W. DUDAS
*Director of the United States Patent and Trademark Office*